(12) United States Patent
Gadot et al.

(10) Patent No.: US 11,927,581 B2
(45) Date of Patent: Mar. 12, 2024

(54) GREENHOUSE GAS EMISSION MONITORING SYSTEMS AND METHODS

(71) Applicant: Cameron International Corporation, Houston, TX (US)

(72) Inventors: Raphael Gadot, Sugar Land, TX (US); Adam Huynh, Richmond, TX (US); Andrew J. Speck, Milton, MA (US); Andrew Emil Pomerantz, Lexington, MA (US); Gocha Chochua, Sugar Land, TX (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 181 days.

(21) Appl. No.: 17/446,845

(22) Filed: Sep. 3, 2021

(65) Prior Publication Data
US 2022/0065834 A1 Mar. 3, 2022

Related U.S. Application Data

(60) Provisional application No. 63/073,958, filed on Sep. 3, 2020.

(51) Int. Cl.
*G01N 33/00* (2006.01)
(52) U.S. Cl.
CPC .................. *G01N 33/0062* (2013.01)
(58) Field of Classification Search
CPC ........... G01N 33/0047; G01N 33/0062; G01N 33/0075; G01N 21/3504; G01N 33/004;
(Continued)

(56) References Cited

U.S. PATENT DOCUMENTS 11,454,622 B2 * 9/2022 Billat .................. G01N 33/0031
2009/0287520 A1 11/2009 Zimmerman
(Continued)

FOREIGN PATENT DOCUMENTS

KR 1020150138941 A 12/2015
KR 20160008781 A 1/2016
(Continued)

OTHER PUBLICATIONS

International Search Report and Written Opinion of PCT Application No. PCT/US2021/048981 dated Dec. 23, 2021, 10 pages.
(Continued)

*Primary Examiner* — Jeffrey P Aiello
(74) *Attorney, Agent, or Firm* — Jeffrey D. Frantz

(57) ABSTRACT

Systems and methods presented herein generally relate to greenhouse gas emission monitoring and, more particularly, to a greenhouse gas emission monitoring workflow using various different types of sensors. For example, a system includes a plurality of sensors located within an oil and gas worksite. At least one sensor of the plurality of sensors is configured to detect a status of equipment at the oil and gas worksite. The system also includes a greenhouse gas emission analysis system configured to receive sensor data from the plurality of sensors. The greenhouse gas emission analysis system is also configured to correlate the sensor data from the plurality of sensors (e.g., using one or more reduced order models (ROMs) that reduce the computational complexity of computational fluid dynamics model simulations of previously collected data relating to operation of the oil and gas worksite). The greenhouse gas emission analysis system is further configured to determine an existence of a greenhouse gas emission within the oil and gas worksite, a location of the greenhouse gas emission within the oil and gas worksite, and a quantity of the greenhouse gas emission
(Continued)

within the oil and gas worksite based at least in part on the correlation.

20 Claims, 5 Drawing Sheets

(58) Field of Classification Search
CPC .......... G01N 33/0031; G01N 33/0036; G01N 33/0004; G01N 21/31; G01N 33/225; G01N 33/0063; G01N 33/0073; G01N 21/359; G01N 2001/021; G01N 33/241; G01N 2030/8854; Y02P 90/84; Y02P 90/02; Y02P 90/80; Y02P 80/20; Y02P 30/00; Y02P 20/151; G06N 20/00; E21B 43/00; G05B 19/4185; Y02A 50/20; G06F 17/18; G06F 18/2178; G06F 2113/08; Y02E 20/32; G01D 21/02
USPC .............. 73/1.06, 23.2, 23.31, 31.01, 31.05; 340/539.26, 540, 632; 356/437; 422/83; 702/2, 12–13, 19, 23–24, 30–32, 45, 702/50–51, 188–189; 703/1–2, 6–7, 9–10
See application file for complete search history.

(56) References Cited

U.S. PATENT DOCUMENTS

| | | | |
|---|---|---|---|
| 2010/0198736 A1 | 8/2010 | Marino | |
| 2011/0040493 A1 | 2/2011 | Choi et al. | |
| 2012/0010917 A1 | 1/2012 | De Godoi | |
| 2013/0246027 A1* | 9/2013 | Rodriguez | G06F 30/23 703/9 |
| 2014/0081579 A1 | 3/2014 | Tyburski | |
| 2015/0185194 A1 | 7/2015 | Prince et al. | |
| 2017/0003684 A1* | 1/2017 | Knudsen | G05D 1/0094 |
| 2017/0097274 A1 | 4/2017 | Thorpe et al. | |
| 2018/0266241 A1* | 9/2018 | Ferguson | E21B 47/13 |
| 2018/0292374 A1* | 10/2018 | Dittberner | G08G 5/0086 |
| 2019/0285600 A1 | 9/2019 | Klein et al. | |
| 2019/0366400 A1 | 12/2019 | Chambers | |
| 2020/0240259 A1* | 7/2020 | Balasubramaniam | E21B 41/00 |
| 2020/0371079 A1* | 11/2020 | Abedini | G01N 27/626 |
| 2022/0008972 A1* | 1/2022 | Quigley | B09C 1/005 |
| 2023/0176023 A1 | 6/2023 | Wong | |

FOREIGN PATENT DOCUMENTS

| | | | | |
|---|---|---|---|---|
| KR | 20200074648 A | 6/2020 | | |
| WO | WO-2016089979 A1 * | 6/2016 | .............. | E04B 1/74 |
| WO | 2023033832 A1 | 3/2023 | | |
| WO | 2023108041 A1 | 6/2023 | | |

OTHER PUBLICATIONS

International Search Report and Written Opinion of PCT Application No. PCT/US2021/048977 dated Jun. 3, 2022 9 pages.
International Search Report and Written Opinion of the PCT Application No. PCT/US2022/081142 dated Apr. 25, 2023, 12 pages.
Alvarez, et al. "Assessment of methane emissions from the US oil and gas supply chain." Science 361.6398 (2018): 186-188.
Stockie, John M. "The mathematics of atmospheric dispersion modeling." Siam Review 53.2 (2011): 349-372.
Briggs, G. A. "Optimum formulas for buoyant plume rise." Philosophical Transactions of the Royal Society of London. Series A, Mathematical and Physical Sciences 265.1161 (1969): 197-203.
Hanna et al., Handbook on atmospheric diffusion. No. DOE/TIC-11223. National Oceanic and Atmospheric Administration, Oak Ridge, TN (USA). Atmospheric Turbulence and Diffusion Lab., 1982.
Epa ISC3 method, https://www.epa.gov/scram/air-quality-dispersion-modeling-alternative-models#isc3 (16 pages).
EPA OTM33a method, https://www.epa.gov/emc/emc-other-test-methods#Other%20Test%20Methods (20 pages).
Fugitive Emissions Abatement Simulation Testbed (FEAST) software, https://github.com/EAOgroup/FEAST (6 pages).
Seinfeld et al., Atmospheric chemistry and physics: from air pollution to climate change. John Wiley & Sons, 2016, Sections 18.10-18.11, pp. 859-868.
Turner, D. Bruce. Workbook of atmospheric dispersion estimates: an introduction to dispersion modeling. CRC press, 1994, Sections 2.4-2.9, pp. 2-3 to 2-13.
De Visscher, Alex. Air dispersion modeling: foundations and applications. John Wiley & Sons, 2013, sections 6.3-6.5, pp. 145-152.
Ponish, A., et al., 'Some guidelines for genetic algorithm implementation in MINLP batch plant design', Advances in Metaheuristics for Hard Optimization: p. 293., Springer, 2007.
Whitley, D., 'Next generation genetic algorithms: A users guide', Handbook of Metaheuristics, Springer, 2019, p. 245-274.

* cited by examiner

GREENHOUSE GAS EMISSION MONITORING SYSTEMS AND METHODS

CROSS-REFERENCE TO RELATED APPLICATION

This application claims priority to and the benefit of U.S. Provisional Patent Application Ser. No. 63/073,958, entitled "Greenhouse Gas Emission Monitoring Workflow Using Discrete Sensors," filed Sep. 3, 2020, which is hereby incorporated by reference in its entirety for all purposes.

BACKGROUND

The present disclosure generally relates to greenhouse gas emission monitoring and, more particularly, to a greenhouse gas emission monitoring workflow using various different types of sensors.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Methane is a relatively potent greenhouse gas and the main component of natural gas. The process of extracting and processing natural gas inevitably results in some methane emissions, and those emissions lead to global warming, contributing significantly to climate change. As such, operators in upstream/midstream oil and gas are interested in reducing methane emissions from their facilities. Such emissions arise from a range of facilities (e.g., single wells to gas plant), sources (e.g., intentional vents to unintentional fugitive leaks), and equipment (e.g., tanks, compressors, valves, pneumatic controllers, and so forth). Thus, methane emissions can be reduced by a variety of technologies including leak detection, leak repair, venting elimination, and data management. Indeed, numerous, diverse technologies are available to measure and to reduce such emissions, particularly from facilities in the upstream and midstream industries. However, greenhouse gas monitoring often includes the direct measurement of greenhouse gas emissions and levels. There is a need to provide accurate measurement and monitoring of greenhouse gases both from a regulatory perspective and to improve performance within the oil and gas industry.

SUMMARY

A summary of certain embodiments described herein is set forth below. It should be understood that these aspects are presented merely to provide the reader with a brief summary of these certain embodiments and that these aspects are not intended to limit the scope of this disclosure.

Certain embodiments of the present disclosure include a method that includes receiving, via a greenhouse gas emission analysis system, sensor data from a plurality of sensors located within an oil and gas worksite. At least one sensor of the plurality of sensors is configured to detect a status of equipment at the oil and gas worksite. The method also includes correlating, via the greenhouse gas emission analysis system, the sensor data from the plurality of sensors (e.g., using one or more reduced order models (ROMs) that reduce the computational complexity of computational fluid dynamics model simulations of previously collected data relating to operation of the oil and gas worksite). The method further includes determining, via the greenhouse gas emission analysis system, an existence of a greenhouse gas emission within the oil and gas worksite, a location of the greenhouse gas emission within the oil and gas worksite, and a quantity of the greenhouse gas emission within the oil and gas worksite based at least in part on the correlation.

Certain embodiments of the present disclosure also include an edge device that is part of a cloud-based computing environment. The edge device includes a greenhouse gas emission analysis system configured to receive sensor data from a plurality of sensors located within an oil and gas worksite. At least one sensor of the plurality of sensors is configured to detect a status of equipment at the oil and gas worksite. The greenhouse gas emission analysis system is also configured to correlate the sensor data from the plurality of sensors (e.g., using one or more ROMs that reduce the computational complexity of computational fluid dynamics model simulations of previously collected data relating to operation of the oil and gas worksite). The greenhouse gas emission analysis system is further configured to determine an existence of a greenhouse gas emission within the oil and gas worksite, a location of the greenhouse gas emission within the oil and gas worksite, and a quantity of the greenhouse gas emission within the oil and gas worksite based at least in part on the correlation.

Certain embodiments of the present disclosure also include a system that includes a plurality of discrete sensors located within an oil and gas worksite. At least one sensor of the plurality of sensors is configured to detect a status of equipment at the oil and gas worksite. The system also includes a greenhouse gas emission analysis system configured to receive sensor data from the plurality of discrete sensors. The greenhouse gas emission analysis system is also configured to correlate the sensor data from the plurality of discrete sensors using one or more ROMs that reduce the computational complexity of computational fluid dynamics model simulations of previously collected data relating to operation of the oil and gas worksite. The greenhouse gas emission analysis system is further configured to determine an existence of a greenhouse gas emission within the oil and gas worksite, a location of the greenhouse gas emission within the oil and gas worksite, and a quantity of the greenhouse gas emission within the oil and gas worksite based at least in part on the correlation.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which.

DETAILED DESCRIPTION

Figure 1:
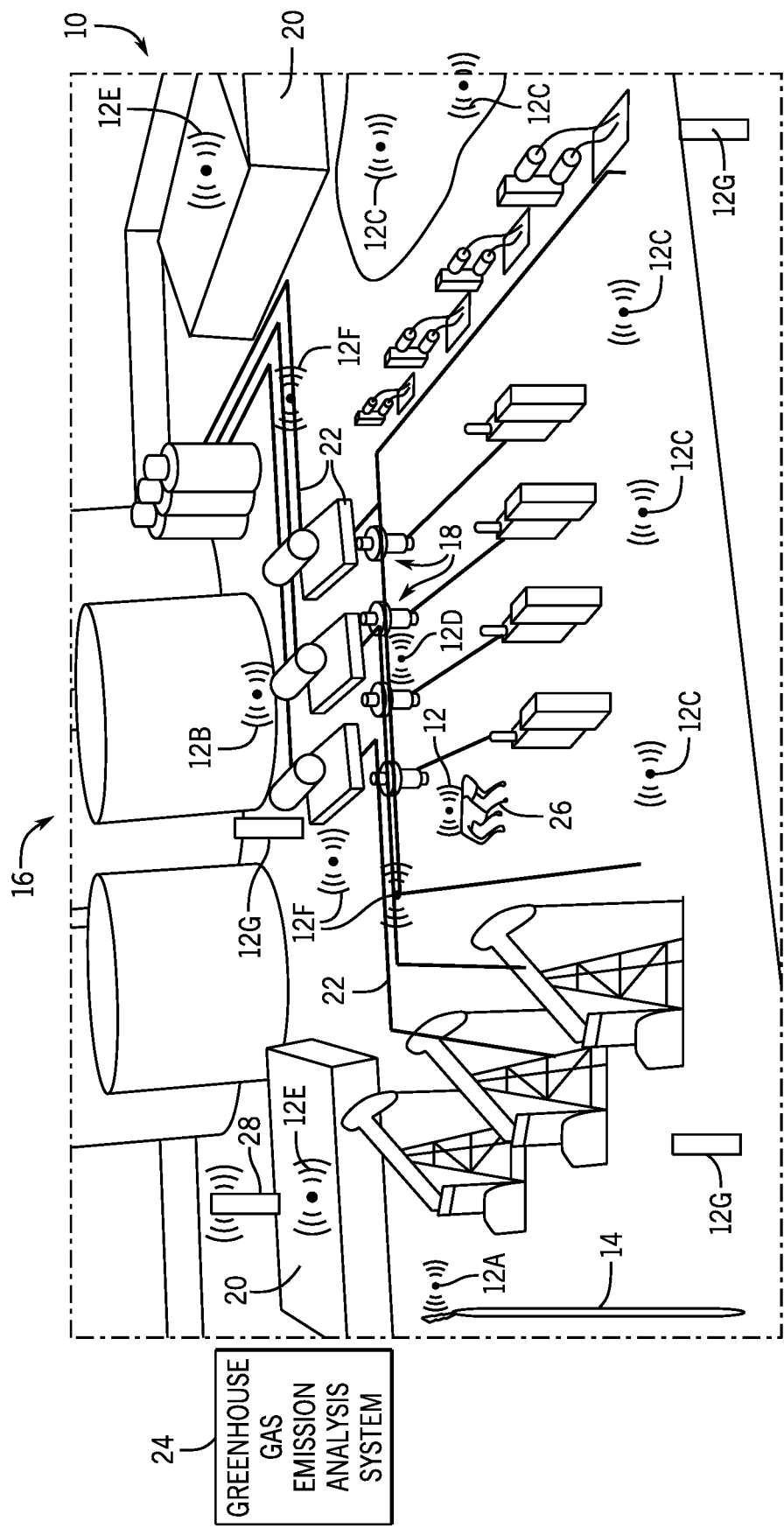
FIG. 1 illustrates an example oil and gas worksite that may include a plurality of sensors that may be used to monitor greenhouse gas emissions at an oil and gas worksite, in accordance with embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements."

In addition, as used herein, the terms "real time", "real-time", or "substantially real time" may be used interchangeably and are intended to described operations (e.g., computing operations) that are performed without any human-perceivable interruption between operations. For example, as used herein, data relating to the systems described herein may be collected, transmitted, and/or used in control computations in "substantially real time" such that data readings, data transfers, and/or data processing steps occur once every second, once every 0.1 second, once every 0.01 second, or even more frequent, during operations of the systems (e.g., while the systems are operating). In addition, as used herein, the terms "automatic" and "automated" are intended to describe operations that are performed are caused to be performed, for example, by a greenhouse gas emission analysis system (i.e., solely by the greenhouse gas emission analysis system, without human intervention).

An aspect of the present disclosure is to enable the identification of fugitive methane emissions. Fugitive emissions of natural gas are economically and environmentally detrimental because the emitted gas is lost from the production stream and because methane (i.e., the main component of natural gas) is a relatively potent greenhouse gas. Current methods of emission detection are relatively expensive, as they generally require either a large amount of manpower or expensive equipment to detect gas leaks. Moreover, current methods are not fully effective since every piece of oilfield equipment (from the well head to refineries and process plants) that holds gas needs to be checked for fugitive emissions. The most common current methods of detection are periodic checks, which are often unable to detect if a gas leakage has occurred between the check points. Additionally, determining whether a specific release of methane is planned or an accidental release is critical for identifying the correct response, which is difficult with current methodologies.

Another aspect of the present disclosure is to monitor greenhouse gas emissions using permanently (or, at least, semi-permanently) installed discrete sensors. In particular, certain embodiments described herein provide a comprehensive suite of connected services to monitor and remediate greenhouse gas emissions. Many greenhouse gas detection technologies rely on Optical Gas Imaging (OGI), or sniffers, which require human intervention. Certain embodiments described herein include permanently (or, at least, semi-permanently) installed discrete sensors distributed throughout a worksite to detect greenhouse gas emissions.

FIG. 1 illustrates an example oil and gas worksite 10 that may include a plurality of sensors 12 that may be used to monitor greenhouse gas emissions at the oil and gas worksite 10. For example, as illustrated in FIG. 1, in certain embodiments, the sensors 12 may include flare monitors 12A, tank sensors 12B, gas concentration monitors 12C, compressor health monitors 12D, structural monitors 12E, process monitors 12F, and/or meteorological sensors 12G. However, in other embodiments, the sensors 12 may include other types of sensors capable of providing data relating to greenhouse gas emissions. Furthermore, other types of data may be used to monitor greenhouse gas emissions at the oil and gas worksite 10 such as the time of day when the detection occurred and the sunrise/sunset time on that day, among other information.

In certain embodiments, one or more flare monitors 12A may be used to monitor flaring of one or more flares 14 at the oil and gas worksite 10 in order to prevent methane emissions by combusting methane into carbon dioxide. In certain embodiments, the one or more flare monitors 12A may be installed on, or in close proximity to (e.g., within a few feet of), the one or more flares 14. Substantial methane emissions may occur if flares 14 are unlit or burn inefficiently. The flares 14 may be monitored by many various types of flare monitors 12A. For example, in certain embodiments, the flare monitors 12A may include one or more cameras, which may detect the absence of a flame from a particular flare 14, indicating that the particular flare 14 is unlit. In certain embodiments, the one or more cameras may detect the presence of black smoke emanating from a particular flare 14, indicating inefficient combustion via the particular flare 14. In addition, in certain embodiments, the flare monitors 12A may include one or more thermocouples or other temperature sensors, which may detect temperatures relating to a particular flare 14, indicating that the particular flare 14 is unlit or combusting inefficiently. In addition, in certain embodiments, the flare monitors 12A may include one or more light sensors configured to detect light proximate to a particular flare 14. In addition, in certain embodiments, the flare monitors 12A may include one or more carbon dioxide sensors to detect carbon dioxide concentrations in the vicinity around a particular flare 14. Low carbon dioxide concentrations in the vicinity of the particular flare 14 may indicate that the particular flare 14 is unlit or combusting inefficiently. In addition, in certain embodiments, the flare monitors 12A may include one or more flow sensors to detect a flow of gas into a particular flare 14. Low flow into the particular flare 14 may indicate that the particular flare 14 is not destroying as much methane as usual. Any of this non-limiting list of conditions relating to operation of flares 14 may be correlated with other data described herein to indicate that unintentional greenhouse gas emissions may be occurring relating to the flares 14.

In certain embodiments, one or more tank sensors 12B may be used to monitor operational statuses of one or more storage tanks 16 (e.g., oil or water storage tanks) at the oil and gas worksite 10. In certain embodiments, the one or more tank sensors 12B may be installed on, or in close proximity to (e.g., within a few feet of), the one or more storage tanks 16. Oil or water storage tanks are also a common source of methane emissions. These emissions can occur, for example, when a thief hatch on a storage tank 16 is left open or when a pressure relief valve of the storage tank 16 is opening too frequently. As such, in certain embodiments, the tank sensors 12B may detect whether certain hatches of certain storage tanks 16 are opened or closed, whether (and how often) certain valves of certain storage tanks 16 are opened or closed, as well as other operational statuses of the storage tanks 16. In certain embodiments, the tank sensors 12B may include one or more contact sensors to detect when certain hatches of certain storage tanks 16 are opened or closed. In addition, in certain embodiments, the tank sensors 12B may include one or more cameras to detect when certain hatches of certain storage tanks 16 are opened or closed. In addition, in certain embodiments, the tank sensors 12B may include one or more tank pressure gauges and/or level gauges to detect tank pressures within certain storage tanks 16 and/or tank levels (e.g., of water or gas stored in certain storage tanks 16), which may indicate whether a pressure relief valve is operating appropriately. Any of this non-limiting list of conditions relating to operation of storage tanks 16 may be correlated with other data described herein to indicate that unintentional greenhouse gas emissions may be occurring relating to the storage tanks 16.

In certain embodiments, one or more gas concentration monitors 12C may be used to directly monitor gas concentrations at certain locations within the oil and gas worksite 10. In certain embodiments, the gas concentration monitors 12C may be used without other sensors to monitor for emissions. However, as described in greater detail herein, in other embodiments, the other sensors 12 described herein may be used to supplement the gas concentration readings detected by the gas concentration monitors 12C. While the gas concentration monitors 12C can in theory be used to identify any source of methane emissions, in practice, there may be some constraints that need to be considered. For example, emissions from storage tanks 16 often occur from elevated locations, so a gas concentration monitor 12C should also be elevated to maximize sensitivity. However, there is often little room, particularly outside a hazardous zone, to mount a gas concentration monitor 12C. Similarly, gas concentration monitors 12C should, ideally, be located relatively far away from flares 14 to avoid being damaged by the heat from the flares 14; however, the sensitivity of methane concertation monitors 12C decreases at greater distances. In certain embodiments, the gas concentration monitors 12C may be primarily used to monitor for greenhouse gas emissions from sources other than flares 14 or storage tanks 16. In certain embodiments, the gas concertation monitors 12C may include photoacoustic sensors, metal oxide sensors, catalytic sensors, solid state sensors, infrared spectrometers, molecular property spectrometers (MPSs), microelectromechanical systems (MEMS) sensors, interband cascade light emitting devices, or any other sensors configured to directly detect greenhouse gas concentrations. Depending on the sensor type, the gas concentration monitors 12C may convert a measured variable to an electrical signal using chemical, physical, or other processes.

In certain embodiments, one or more compressor health monitors 12D may be used to monitor certain operational statuses of one or more compressors 18 at the oil and gas worksite 10. In certain embodiments, the compressor health monitors 12D may be installed on, or in close proximity to (e.g., within a few feet of), the one or more compressors 18. By determining the operational statuses of certain compressors 18, the compressor health monitors 12D may provide additional information as to whether valves, seals, motors, or other equipment associated with the compressors 18 are near failure. If a problem is detected at the same time as elevated greenhouse gas concentrations, there is an increased likelihood of a gas leak occurring. Although described herein as being compressor health monitors 12D configured to detect operational statuses of compressors 18, in other embodiments, pump health monitors configured to detect operational statuses of pumps at the oil and gas worksite 10 may also be used. Any of this non-limiting list of conditions relating to operational statuses of compressors 18 (or pumps) may be correlated with other data described herein to indicate that unintentional greenhouse gas emissions may be occurring relating to the compressors 18 (or pumps).

In certain embodiments, one or more structural monitors 12E may be used to monitor one or more structures 20 at the oil and gas worksite 10, for example, as they evolve over time. In certain embodiments, the structural monitors 12E may be installed on, or in close proximity to (e.g., within a few feet of), the one or more structures 20. For example, in certain embodiments, the structural monitors 12E may include light detection and ranging (LIDAR) devices and/or cameras (e.g., either infrared or visible light cameras) configured to collect three-dimensional (3D) scanning and images and/or video of the oil and gas worksite 10, the data relating to which may be used to generate 3D reconstructions of structures 20 at the oil and gas worksite 10, as well as other equipment at the oil and gas worksite 10 and other physical features of the oil and gas worksite 10 that can be reconstructed in a 3D model. In certain embodiments, by comparing the locations at which elevated greenhouse gas concentrations are measured to locations of different structures 20, a better prediction as to the location of a possible gas leak may be generated.

In certain embodiments, one or more process monitors 12F may be used to monitor certain processes carried out by certain processing equipment 22 (e.g., valves, pipes, heat exchangers, manifolds, mixing chambers, and so forth) of the oil and gas worksite 10. For example, the infrastructure of the oil and gas worksite 10 may include process monitors 12F configured to measure operational parameters, such as valve positions, flow rates of fluids (e.g., oil and gas), and other common operational parameters relating to certain processes that occur at the oil and gas worksite 10. When combined with knowledge of the process architecture, this information may be used to determine whether greenhouse gas is expected to be released due to a current configuration of the processes. In certain embodiments, the process monitors 12F may already exist at the oil and gas worksite 10 or could be added for both understanding day-to-day operations as well as enhancing gas leak detection, as described in greater detail herein.

In certain embodiments, one or more meteorological sensors 12G may be used to collect certain meteorological data relating to the oil and gas worksite 10. For example, in certain embodiments, anemometers measuring wind direction, speed, and stability class may be used to infer the dispersion of a gas plume and, thus, more precisely infer a greenhouse gas emission location. In addition, in certain embodiments, other types of meteorological data may be collected by the meteorological sensors 12G including, but not limited to, solar radiation, precipitation, temperature, and humidity, all of which may play a role in the methane plume behavior, as well as the sensor calibration. At a minimum, using such meteorological sensors 12G may enable determining whether a greenhouse gas emission is occurring within the oil and gas worksite 10 or from a disturbance outside of the oil and gas worksite 10 (e.g., from natural decay sources or external equipment such as vehicles).

Although described primarily herein as pertaining to oil and gas worksites 10, the term "oil and gas worksite" is intended to include any worksites 10 wherein oil and/or gas is processed in any manner, and from which fugitive gas emissions may occur. Indeed, the embodiments described herein include systems and methods for identifying fugitive gas emissions from any types of worksites 10 including, but not limited to, emissions of natural gas from well pad equipment or any point in delivery of gas to a point of use. In addition, the embodiments described herein may be applied to other types of gases or fluids emitted from other types of worksites 10. In general, the embodiments described herein include placing one or more sensors 12 described above around an oil and gas worksite 10 as illustrated in FIG. 1. Collectively, the sensors 12 provide continuous measurement of fugitive and vented greenhouse gas emissions with respect to the oil and gas worksite 10. In certain embodiments, greenhouse gas concertation data, along with wind data, may be interpreted using an algorithm to determine when an emission occurred, where it occurred, and how large it was (e.g., in terms of units of flow). Optionally, in certain embodiments, machine learning techniques may be used to determine why the emissions occurred.

The embodiments described herein implement a variety of methods for detecting fugitive gas emissions. For example, in some situations, point sensors based on flame ionization detector, metal oxide, or catalytic technology may be used. These sensors may be placed next to (e.g., typically within 1 foot of) potential gas leak sources and measure a local concentration of greenhouse gases. If the concentration exceeds a threshold (e.g., such as 100 ppm above background), the equipment being tested is considered to have a gas leak. This method is typically effective but is relatively inefficient and expensive. In other situations, LIDAR devices and/or cameras (e.g., infrared cameras, visible light cameras, and so forth) may be used to survey a relatively large area for gas leaks. This method can be efficient, but the sensitivity is relatively poor and dependent on external conditions. In addition, the greenhouse gas measurement is often qualitative by comparison. In other situations, sensors may be mounted to mobile platforms such as unmanned aerial vehicles, mobile robots, and so forth. This method can be relatively effective, but can provide intermittent inspection, meaning it can be relatively inaccurate for detecting transient greenhouse gas emission events. In other situations, other permanent solutions can be deployed on location, solving the problem of transient greenhouse gas leaks. Such systems may include technologies such as multipass infrared spectroscopy and metal oxide sensors. Those sensors can be relatively effective but suffer from relatively high costs, relatively short lifetimes, and relatively high-power consumption.

The embodiments described herein combine the best aspects of these methods while minimizing the drawbacks. In particular, in order to improve the performance of systems deployed to identify greenhouse gas emissions from upstream and midstream facilities, the embodiments described herein use multiple different types of sensors 12, operated together to identify and classify methane emissions. In certain embodiments, multiple technologies may be used at the same oil and gas worksite 10, and different technologies (or different combinations of technologies) may be used on different oil and gas worksites 10. As each sensor type provides complementary information, the combination of data from all sensors 12 can significantly improve the performance of the overall system by increasing sensitivity, reducing false positives (e.g., gas vents misclassified as gas leaks) and negatives (e.g., gas leaks misclassified as gas vents), and allowing for better identification of the equipment producing the gas emissions. As described above, there are several different classes of sensors 12 that can be used together in this purpose. For example, in certain embodiments, at least one sensor 12 that is being used (e.g., the flare monitors 12A, the tank sensors 12B, the compressor health monitors 12D, the structural monitors 12E, the process monitors 12F, and so forth) may be configured to detect a status of equipment at the oil and gas worksites 10, as opposed to directly detecting gas emissions (e.g., the gas concentration monitors 12C).

The goal of the sensing is to use a greenhouse gas emission analysis system 24 to estimate when a greenhouse gas emission occurs, where the emission occurs, why the emission occurs (e.g., differentiating gas leaks from gas vents), how large the emission is (e.g., measured in units of flow rate), along with an estimate of the uncertainty of each of these properties including the probability of a gas leak actually occurring. The procedure involves deploying one or more sensors 12 at one or more oil and gas worksites 10 and providing data collected by the sensors 12 to the greenhouse gas emission analysis system 24 for analysis. For example, in certain embodiments, flare monitors 12A and tank sensors 12B may be used to measure emissions from flares 14 and storage tanks 16, respectively, which are relatively difficult to cover with gas concertation sensors 12C. As such, the flare monitors 12A and tank sensors 12B (as well as the compressor health monitors 12D, the structural monitors 12E, the process monitors 12F, and so forth) detect statuses of equipment at the one or more oil and gas worksites 10 to indirectly infer gas emissions at the one or more oil and gas worksites 10, whereas the gas concertation sensors 12C directly detect gas emissions at the one or more oil and gas worksites 10. In certain embodiments, one or more (or, in some applications, fewer) gas concentration sensors 12C may directly detect gas emissions from sources other than flares 14 and storage tanks 16. The flare, tank, and other concertation measurements, along with wind measurements in certain embodiments, may be used as inputs into one or more algorithms executed by the greenhouse gas emission analysis system 24, which may output the timing, location, and magnitude of any detected greenhouse gas emissions, as described in greater detail herein. In certain embodiments, the algorithms may include Gaussian plume models, Lagrangian dispersion models, reverse dispersion models, computational fluid dynamics simulations, or other inversion models. Optionally, in certain embodiments, patterns in the time series of greenhouse gas emission rate or between greenhouse gas emission rates and equipment characteristics may be used by the greenhouse gas emission analysis system 24 to determine if the emissions were intended (i.e., vent) or unintended (i.e., fugitive). In certain embodiments, this determination may involve methods in data science such as machine learning and artificial intelligence.

When a greenhouse gas emission has been detected and characterized by the greenhouse gas emission analysis system 24 using this approach, the equipment allowing the emissions may be repaired. Furthermore, in certain embodiments, when certain patterns describing greenhouse gas emissions are discovered by the greenhouse gas emission analysis system 24, future emissions may be preemptively prevented by the greenhouse gas emission analysis system 24 by automatically applying these patterns to future sensor detections.

As will be appreciated, there are several different workflows (e.g., including several different combinations of different sensors 12) that can be used and considered for analysis by the greenhouse gas emission analysis system 24. In addition, as illustrated in FIG. 1, in certain embodiments, one or more of the sensors 12 described herein may be mounted to a mobile platform 26, for example, an unmanned aerial vehicle (e.g., a drone), a mobile robot (e.g., a Spot robot), or any other relatively agile mobile platform configured to move about an oil and gas worksite 10, carrying one or more sensors 12 that can detect relevant data relating to greenhouse gas emissions that may be occurring at the oil and gas worksite 10, as described in greater detail herein. In one non-limiting example, if a LIDAR and/or visible camera (e.g., as a structural monitor 12E) is mounted to a mobile platform 26 moving about the oil and gas worksite 10, both a 3D reconstruction of the infrastructure of the oil and gas worksite 10 and a corresponding 3D visualization of a gas plume for a possible gas leak may be generated by the greenhouse gas emission analysis system 24. This information thus allows clear determination by the greenhouse gas emission analysis system 24 of where the gas leak source is and confirmation that it is coming from the oil and gas worksite 10 itself.

Another example workflow that may be implemented by the greenhouse gas emission analysis system 24 is to correlate gas concentration time series (e.g., as collected by the gas concentration monitors 12C) together with events detected by other monitors like tank sensors 12B or compressor health monitors 12D. If elevated gas concentration readings occur at the same time as another sensor 12 detecting that there is some operational change (e.g., a thief hatch of a storage tank 16 being opened), then the greenhouse gas emission analysis system 24 may infer that it is likely that a gas leak is occurring where the operational change is occurring. In certain embodiments, this analysis by the greenhouse gas emission analysis system 24 may be enhanced using standard sensor fusion techniques such as Kalman filtering, particle filtering, Bayesian inference, and so forth. Additionally, in certain embodiments, this information may be correlated by the greenhouse gas emission analysis system 24 with information such as planned maintenance operations and data from standard process instrumentation sensors (e.g., the process monitors 12F) to determine whether a specific release is accidental or a controlled release that is expected.

As described in greater detail herein, in certain embodiments, the greenhouse gas emission analysis system 24 may interpret data received from an array of distributed discrete gas concentration monitors 12C (e.g., configured to detect concentrations of methane, volatile organic compounds (VOCs), carbon dioxide ($CO_2$), and so forth) as well as other sensors 12 located around an oil and gas worksite 10 for the purpose of determining an origin location of a greenhouse gas emission and quantifying the greenhouse gas emission (e.g., an amount of the greenhouse gas emission, a direction of dispersion of the greenhouse gas emission, and so forth). As such, the embodiments described herein enable the determination of the amount of greenhouse gas emissions from facilities in terms of cost and environmental footprint. Since the sensors 12 may be permanently (or, at least, semi-permanently) located within the oil and gas worksite 10 and connected to the cloud, operators of the oil and gas worksite 10 may have access in substantially real time to emission information without having to involve any human intervention (e.g., thereby resulting in less health and safety exposure).

As illustrated in FIG. 1, in certain embodiments, some or all of the sensors 12 may be configured to communicate wirelessly to the greenhouse gas emission analysis system 24 for the purpose of communicating the data collected by the sensors 12 for analysis by the greenhouse gas emission analysis system 24, as described in greater detail herein. In addition, as also illustrated, in certain embodiments, one or more communications gateways 28 may be located around the oil and gas worksite 10 and may be used to facilitate communication between the sensors 12 and the greenhouse gas emission analysis system 24 by, for example, relaying data to the greenhouse gas emission analysis system 24 from the sensors 12. For example, in certain embodiments, the greenhouse gas emission analysis system 24 may be implemented as an edge device that is part of a cloud-based computing environment, and the gateway 28 may facilitate communication of sensor data from the sensors 12 to the greenhouse gas emission analysis system 24 via the cloud.

Figure 2C:
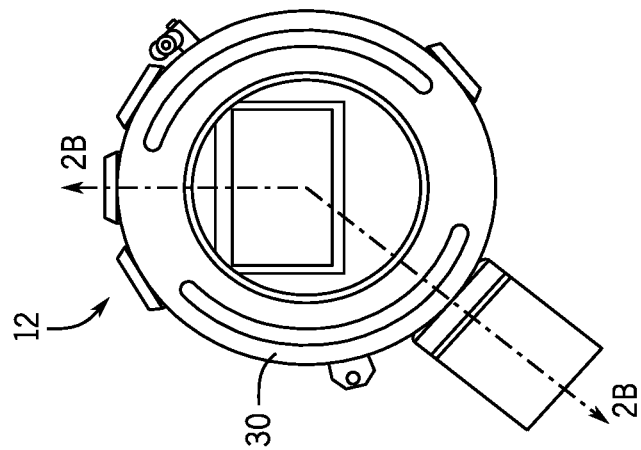
FIGS. 2A through 2C illustrate various views of exemplary packaging of discrete sensors, in accordance with embodiments of the present disclosure.
Figure 2B:
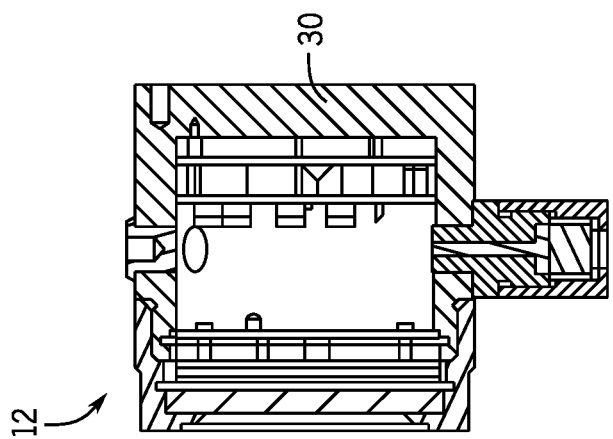
Figure 2A:
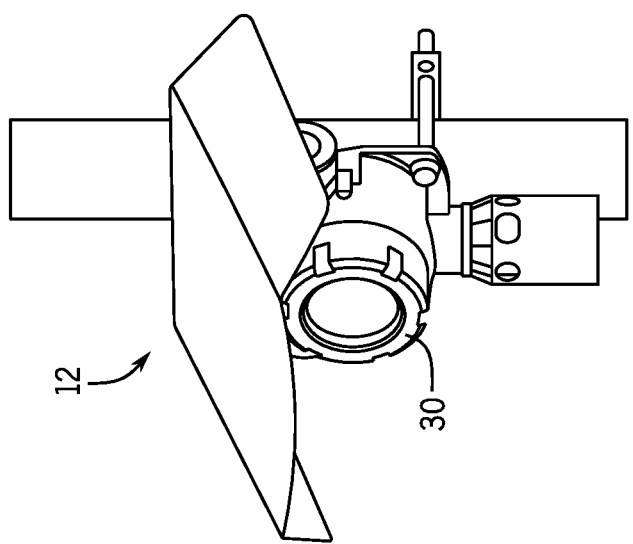

As described above with respect to FIG. 1, in certain embodiments, some of the sensors 12 described herein may be permanently (or, at least, semi-permanently) affixed at particular locations of the oil and gas worksite 10 and/or to particular equipment of the oil and gas worksite 10 while other sensors 12 may be attached to mobile platforms 26, which are configured to maneuver the sensors 12 around the oil and gas worksite 10. As used herein, the term "discrete sensor" may refer to an individual sensor or set of sensors that are packaged in an enclosure that protects the sensors from environmental factors. FIGS. 2A through 2C illustrate various views of exemplary packaging of discrete sensors 12 described herein that are permanently (or, at least, semi-permanently) affixed at particular locations of the oil and gas worksite 10 and/or to particular equipment of the oil and gas worksite 10. As illustrated, in certain embodiments, the packaging of the sensors 12 generally includes a hermetic enclosure 30 within which the electronic components associated with the individual sensors may be disposed.

As described in greater detail herein, the greenhouse gas emission analysis system 24 is configured to detect the existence of a greenhouse gas emission within the oil and gas worksite 10, to automatically determine a location of the greenhouse gas emission within the oil and gas worksite 10, and to quantify the greenhouse gas emission based on data collected by the sensors 12 described herein. In particular, the greenhouse gas emission analysis system 24 is configured to receive data from a plurality of different types of sensors 12, to automatically correlate the various types of data collected by the sensors 12, and to identify patterns within the correlated data to detect the existence of a greenhouse gas emission within the oil and gas worksite 10, to automatically determine a location of the greenhouse gas emission within the oil and gas worksite 10, and to quantify the greenhouse gas emission. In addition, the greenhouse gas emission analysis system 24 is further configured to identify whether the greenhouse gas emission is a gas leak (e.g., unintentional) or a gas vent (e.g., intentional), for example, based at least in part on correlations between the determined gas emission and operational data, which may indicate that the gas emission was, indeed, expected.

In addition, in certain embodiments, in response to detecting a particular gas leak, the greenhouse gas emission analysis system 24 may automatically send one or more control signals to one or more pieces of equipment (e.g., the flares 14, the storage tanks 16, the compressors 18 (or pumps), the processing equipment 22, the mobile platforms 26, and so forth) of the oil and gas worksite 10 such that one or more operational parameters of the one or more pieces of equipment may be automatically adjusted to minimize (e.g., mitigate) the effects of the detected gas leak. For example, if the greenhouse gas emission analysis system 24 determines that a gas leak is likely due to a particular valve opening too much, the greenhouse gas emission analysis system 24 may automatically send a control signal to the particular valve to cause the particular valve to close.

Figure 3:
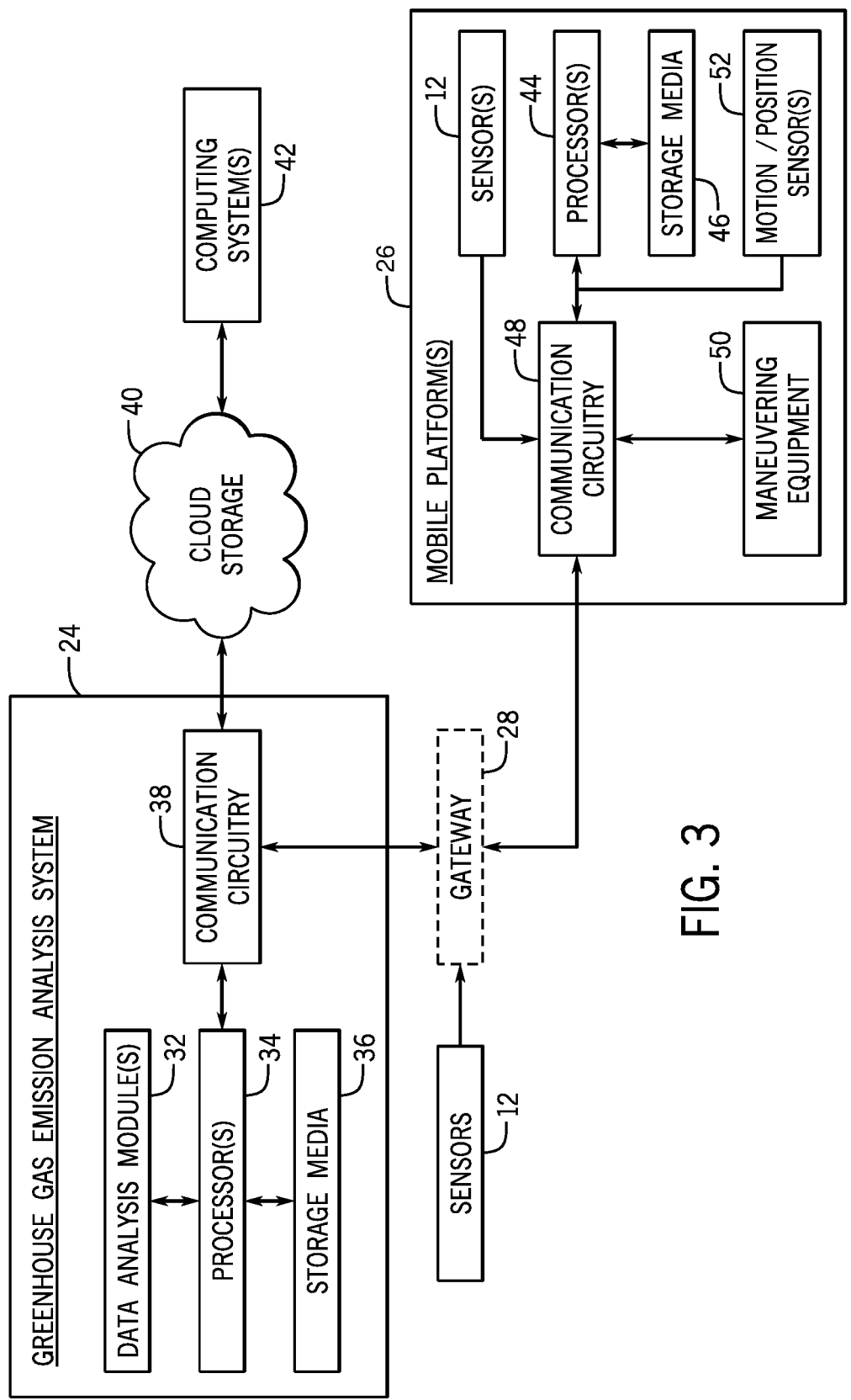
FIG. 3 illustrates how a greenhouse gas emission analysis system interacts with various components of the oil and gas worksite of FIG. 1, in accordance with embodiments of the present disclosure.

As illustrated in FIG. 3, in certain embodiments, the greenhouse gas emission analysis system 24 described herein may include one or more data analysis modules 32 (e.g., programs of computer-executable instructions and associated data) that may be configured to perform various functions of the embodiments described herein. In certain embodiments, to perform these various functions, a data analysis module 32 executes on one or more processors 34 of the greenhouse gas emission analysis system 24, which may be connected to one or more storage media 36 of the greenhouse gas emission analysis system 24. Indeed, in certain embodiments, the one or more data analysis modules 32 may be stored in the one or more storage media 36 of the greenhouse gas emission analysis system 24.

In certain embodiments, the one or more processors 34 of the greenhouse gas emission analysis system 24 may include a microprocessor, a microcontroller, a processor module or subsystem, a programmable integrated circuit, a programmable gate array, a digital signal processor (DSP), or another control or computing device. Alternatively or additionally, the one or more processors 34 of the greenhouse gas emission analysis system 24 may include discrete electronic components coupled to a printed circuit board, integrated circuitry (e.g., Application Specific Integrated Circuits (ASIC)), and/or programmable logic devices (e.g., a Field Programmable Gate Arrays (FPGA)).

In certain embodiments, the one or more data analysis modules 32 may be implemented as computer program logic for use with the one or more processors 34 of the greenhouse gas emission analysis system 24. The computer program logic may be embodied in various forms, including a source code form or a computer executable form. Source code may include a series of computer program instructions in a variety of programming languages (e.g., an object code, an assembly language, or a high-level language such as C, C++, or JAVA). The computer instructions may be distributed in any form as a removable storage medium with accompanying printed or electronic documentation (e.g., shrink wrapped software), preloaded on the greenhouse gas emission analysis system 24 (e.g., on system ROM or fixed disk), or distributed from a server or electronic bulletin board over a communication system (e.g., the Internet or World Wide Web). In addition, in certain embodiments, the greenhouse gas emission analysis system 24 may be implemented as an edge device that is part of a cloud-based computing environment, and the computer program logic may be executed by the edge device in the cloud-based computing environment.

In certain embodiments, the one or more storage media 36 of the greenhouse gas emission analysis system 24 may be implemented as one or more non-transitory computer-readable or machine-readable storage media. In certain embodiments, the one or more storage media 36 of the greenhouse gas emission analysis system 24 may include one or more different forms of memory including semiconductor memory devices such as dynamic or static random access memories (DRAMs or SRAMs), programmable read-only memories (PROMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); PC cards (e.g., PCMCIA cards), or other types of storage devices.

As described above, in certain embodiments, the computer-executable instructions and associated data of the data analysis module(s) 32 may be provided on one computer-readable or machine-readable storage medium of the storage media 36 of the greenhouse gas emission analysis system 24, or alternatively, may be provided on multiple computer-readable or machine-readable storage media distributed in a large system having possibly plural nodes. Such computer-readable or machine-readable storage medium or media are considered to be part of an article (or article of manufacture), which may refer to any manufactured single component or multiple components. In certain embodiments, the one or more storage media 36 of the greenhouse gas emission analysis system 24 may be located either in the machine running the machine-readable instructions, or may be located at a remote site from which machine-readable instructions may be downloaded over a network for execution. Indeed, in certain embodiments, the greenhouse gas emission analysis system 24 may be implemented as an edge device that is part of a cloud-based computing environment, and the machine-readable instructions may be executed by the edge device in the cloud-based computing environment.

In certain embodiments, the processor(s) 34 of the greenhouse gas emission analysis system 24 may be connected to communication circuitry 38 of the greenhouse gas emission analysis system 24 to allow the greenhouse gas emission analysis system 24 to communicate with the various sensors 12, the mobile platforms 26, and equipment located at the oil and gas worksite 10 for the purpose of automatically detecting the existence of a greenhouse gas emission within the oil and gas worksite 10, automatically determining a location of the greenhouse gas emission within the oil and gas worksite 10, and automatically quantifying the greenhouse gas emission based on data collected by the sensors 12, as described in greater detail herein. In certain embodiments, the communication circuitry 38 of the greenhouse gas emission analysis system 24 may also facilitate the greenhouse gas emission analysis system 24 communicating data to cloud storage 40 (or other wired and/or wireless communication network) to, for example, archive the data or to enable external computing systems 42 to access the data and/or to remotely interact with the greenhouse gas emission analysis system 24.

Regardless of the destination for the communication, in certain embodiments, the processor(s) 34 and/or the communication circuitry 38 may be configured to automatically convert the data that is communicated into a data format suitable for transmit to and use by the particular destination to which the data is transmitted. For example, in certain embodiments, certain types of sensors 12, mobile platforms 26, and/or equipment located at one or more oil and gas worksites 10 may only be capable of receiving and acting upon data in particular data formats. As such, in such scenarios, the processor(s) 34 and/or the communication circuitry 38 may automatically convert data to be transmitted to such sensors 12, mobile platforms 26, and/or equipment into the particular data formats before transmitting the data to the sensors 12, mobile platforms 26, and/or equipment. Such automated data conversion and transmission enables the greenhouse gas emission analysis system 24 to more effectively communicate data to users of the greenhouse gas emission analysis system 24.

In certain embodiments, the communication circuitry 38 of the greenhouse gas emission analysis system 24 may be, include, or be implemented by various types of standard interfaces, such as an Ethernet interface, a universal serial bus (USB), a third generation input/output (3GIO) interface, a wireless interface, a cellular interface, and/or a satellite interface, among others. In certain embodiments, the communication circuitry 38 of the greenhouse gas emission analysis system 24 may also include a communication device, such as a modem or network interface card to facilitate exchange of data with external computing devices via a network (e.g., Ethernet connection, digital subscriber line (DSL), telephone line, coaxial cable, cellular telephone system, satellite, etc.).

In addition, as also illustrated in FIG. 3, in certain embodiments, the one or more mobile platforms 26, which each may have one or more sensors 12 attached to it, may also include one or more processors 44 (e.g., similar to the processors 34 of the greenhouse gas emission analysis system 24) configured to run computer program logic, which may be embodied in various forms (e.g., similar to the data analysis modules 32 of the greenhouse gas emission analysis system 24) and may be stored in storage media 46 of the respective mobile platform 26 (e.g., which may be similar to the storage media 36 of the greenhouse gas emission analysis system 24) to automatically (e.g., autonomously) control maneuvering of the respective mobile platform 26 around the oil and gas worksite 10 for the purpose of repositioning its respective sensors 12 such that the sensors 12 can detect data relating to potential gas leaks at the oil and gas worksite 10.

In certain embodiments, the processor(s) 44 of the mobile platform(s) 26 may be connected to communication circuitry 48 of the respective mobile platform 26 (e.g., which may be similar to the communication circuitry 38 of the greenhouse gas emission analysis system 24) to allow the respective mobile platform 26 to communicate with the greenhouse gas emission analysis system 24, the various sensors 12, other mobile platforms 26, and equipment located at the oil and gas worksite 10 for the purpose of determining how to automatically (e.g., autonomously) maneuver itself around the oil and gas worksite 10 to enable its respective sensors 12 to detect data relating to potential gas leaks at the oil and gas worksite 10. In certain embodiments, the communication circuitry 48 of the mobile platform(s) 26 may also facilitate the of the respective mobile platform 26 to communicate data to the cloud storage 40 (or other wired and/or wireless communication network) to, for example, archive the data or to enable external computing systems 42 to access the data and/or to remotely interact with the respective mobile platform 26.

In certain embodiments, the processor(s) 44 of the mobile platform(s) 26 may execute computer program logic to determine how to automatically (e.g., autonomously) control maneuvering equipment 50 of the respective mobile platform 26 to enable the maneuvering equipment 50 to maneuver the respective mobile platform 26 around the oil and gas worksite 10 for the purpose of repositioning its respective sensors 12 such that the sensors 12 can detect data relating to potential gas leaks at the oil and gas worksite 10. For example, in certain embodiments, a mobile platform 26 may be an unmanned aerial vehicle (e.g., a drone) and the maneuvering equipment 50 may include propellers, motors configured to rotate the propellers at specific speeds, and so forth, configured to enable the unmanned aerial vehicle to maneuver the mobile platform 26 aerially about the oil and gas worksite 10. However, in other embodiments, a mobile platform 26 may be a mobile robot and the maneuvering equipment 50 may include robotic legs, wheels, and so forth, configured to maneuver the mobile platform 26 over the ground and certain structures 20 and/or equipment of the oil and gas worksite 10.

In certain embodiments, the processor(s) 44 of the mobile platform(s) 26 may execute computer program logic to determine how to automatically (e.g., autonomously) control maneuvering equipment 50 of the respective mobile platform 26 based at least in part on one or more motion/position sensors 52 of the respective mobile platform 26. As used herein, the term "motion/position sensor" may refer not only to a sensor configured to detection motion and/or a position, such as accelerometers, gyroscopes, and so forth, but also any and all other types of sensors, such as LIDAR devices and/or cameras, global positioning systems (GPS), and so forth, which may provide feedback data that may be used to determine motion and/or a position of a respective mobile platform 26 relative to the oil and gas worksite 10. In certain embodiments, the greenhouse gas emission analysis system 24 may be configured to automatically send control signals to the mobile platform(s) 26 to at least partially control the maneuvering of a particular mobile platform 26 when, for example, the greenhouse gas emission analysis system 24 determines that certain data relating to a potential gas leak may be useful, and that a particular sensor 12 attached to the particular mobile platform 26 may be capable of collecting such data of interest.

Returning to FIG. 1, in certain embodiments, certain sensors 12 may be installed either next to specific equipment of interest (e.g., such as storage tanks 16, compressors 18, processing equipment 22, and so forth) disposed about an oil and gas worksite 10 in order to detect external gas leaks specifically occurring in the vicinity of this equipment of interest. Alternatively or additionally, certain sensors 12 may be distributed across an oil and gas worksite 10 as an array of sensors. In other words, such distributed sensors 12 may not be located next to specific equipment of interest, but rather may be disposed at various locations spaced about the oil and gas worksite 10 such that triangulation between the sensors 12 may be performed, as described in greater detail herein. Indeed, as described in greater detail herein, in certain embodiments, certain sensors 12 may be attached to mobile platforms 26 that are configured to maneuver the sensors 12 about the oil and gas worksite 10 such that the sensors 12 can collect data from almost any location within the oil and gas worksite 10.

Figure 4:
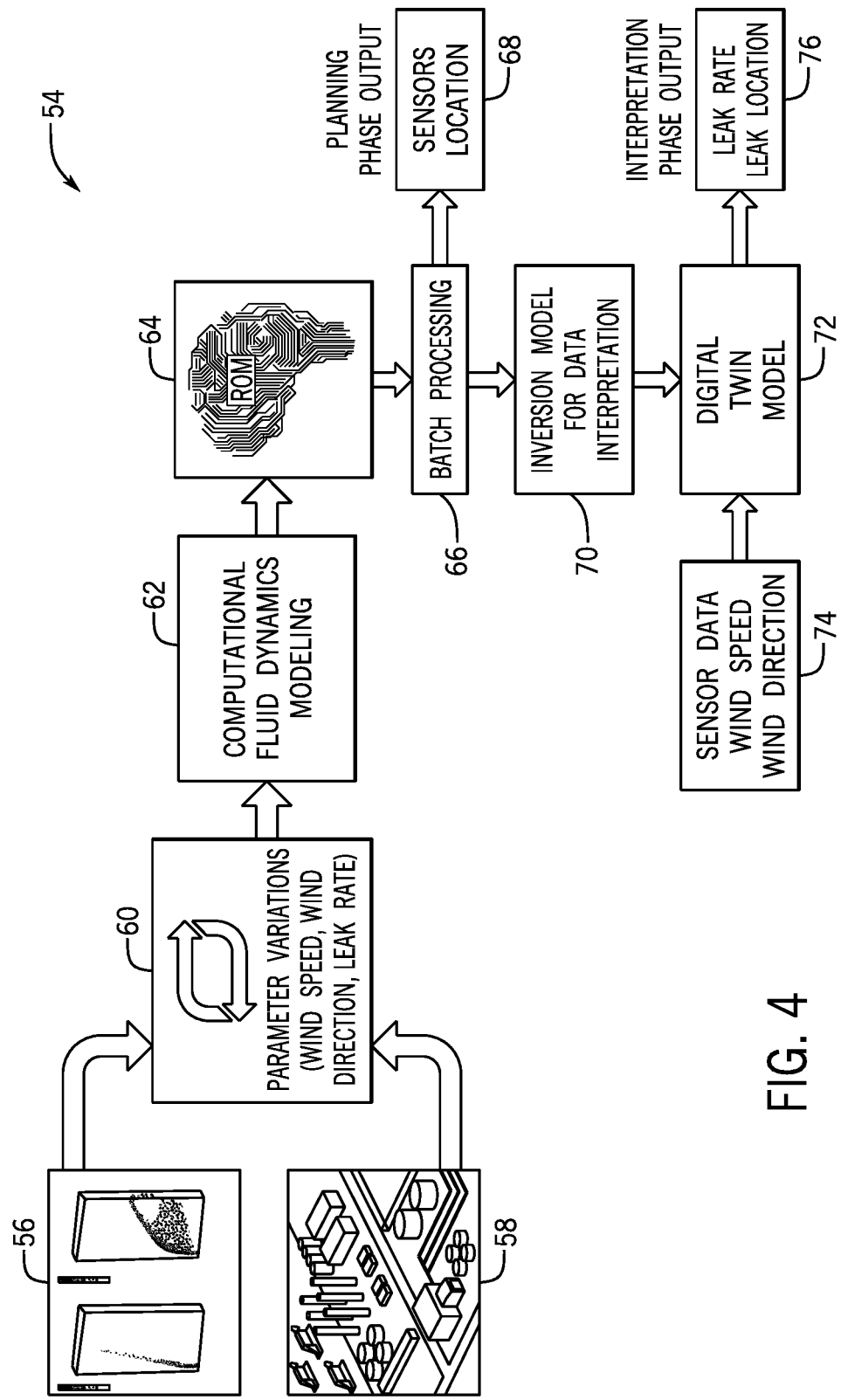
FIG. 4 illustrates an exemplary workflow for quantifying potential gas leaks at the oil and gas worksite of FIG. 1 using computational fluid dynamics (CFD) modeling, in accordance with embodiments of the present disclosure.

Regardless of the specific location (e.g., either fixed or transient) of any given sensor 12 at any given time, each of the sensors 12 may be configured to communicate not only the specific sensor data collected by the respective sensor 12 but also location data for the respective sensor 12 to the greenhouse gas emission analysis system 24 for analysis, as described in greater detail herein. In certain embodiments, based on this location data, the greenhouse gas emission analysis system 24 may triangulate the locations of the sensors 12 from which data is received, and may use this triangulation to quantify any potential gas leaks using computational fluid analytics (CFD) modeling. FIG. 4 illustrates an exemplary workflow 54 for quantifying potential gas leaks at the oil and gas worksite 10 using CFD modeling. For example, in certain embodiments, the CFD modeling may include gas dispersion models, which the greenhouse gas emission analysis system 24 may use to optimize gas sensor deployment and planning, as described in greater detail herein.

As illustrated in FIG. 4, in certain embodiments, the greenhouse gas emission analysis system 24 may generate 3D reconstructions 56 of the oil and gas worksite 10, for example, based on data received from the structural monitors 12E described herein. In addition, in certain embodiments, the greenhouse gas emission analysis system 24 may receive 3D models 58 (e.g., pre-existing computer-aided design (CAD) models) of the oil and gas worksite 10, which have already been generated. In certain embodiments, the greenhouse gas emission analysis system 24 may compare the 3D reconstructions of the oil and gas worksite 10 that are based on the collected sensor data with the pre-existing 3D models of the oil and gas worksite 10 to resolve any differences between the two sets of 3D data. In general, taking the 3D data of the facilities (e.g., structures 20 and other equipment) at the oil and gas worksite 10 into consideration enables the greenhouse gas emission analysis system 24 to take into account the impact of obstructions of objects that will be encountered (e.g., by possible leaked gas as it disperses into the atmosphere) at an oil and gas worksite 10. As described in greater detail herein, in certain embodiments, the variation in height (e.g., at locations where certain sensors 12 are mounted) may also be taken into consideration by the greenhouse gas emission analysis system 24.

Then, in certain embodiments, the greenhouse gas emission analysis system 24 may take into account parameter variations 60, such as wind speed and wind direction (e.g., as detected by the meteorological sensors 12G described herein) as well as in parameters determined by the greenhouse gas emission analysis system 24, such as gas leak rate, gas leak pressure, and so forth. In other words, many of the steps of the workflow 54 illustrated in FIG. 4 may be performed iteratively in substantially real time during operations at the oil and gas worksite 10 such that some of the determined parameters (e.g., gas leak rate, gas leak pressure, and so forth) may be both inputs (e.g., from a previous iterative step) and outputs (e.g., during a current iterative step). In certain embodiments, taking all of the parameter variations 60 into account, the greenhouse gas emission analysis system 24 may utilize gas dispersion modeling in CFD modeling 62 to predict gas dispersion in free space from possible gas leak sources.

In certain embodiments, one or more reduced order models (ROMs) 64 may be generated by the greenhouse gas emission analysis system 24 from the 3D simulation data. In general, the ROMs 64 may enable real-time predictions of a simulation's results when changing a simulation's input variables without having to run the 3D simulation again. One goal of using ROMs 64 is to convert relatively complex CFD models 62 (e.g., which may take a relatively long time to process) to relatively simple analytical models (e.g., which may take only milliseconds, such as less than 100 milliseconds, less than 10 milliseconds, or an even short time period, to process) that may be used to correlate the data collected by the sensors 12, as described in greater detail herein, with reduced computational complexity. As such, a benefit to using ROMs 64 is to reduce the processing time drastically when performing batch simulations. In certain embodiments, over time, batch processing 66 of the ROMs 64 may lead to results, which may be used to plan future locations 68 of the sensors 12. In certain embodiments, the ROMs 64 may be used by the greenhouse gas emission analysis system 24 to construct an inverse model 70 of a predicted gas plume, which may be used by the greenhouse gas emission analysis system 24 for data interpretation. In certain embodiments, the inversion model 70 may then be combined inside a digital twin model 72, which may be configured to receive real-time sensor data from the sensors 12 described herein, as well as wind speed, wind direction, and other environmental parameters, as inputs 74 to automatically determine gas leak locations and gas leak rates as outputs 76.

In general, two main activities of the workflow 54 are the planning phase 68 and the interpretation phase 76. The planning phase 68 may be performed using forward modeling, as described herein. The goal is to optimize, for example, the placement of the sensors 12 in a target oil and gas worksite 10. As described in greater detail herein, historical data may be used to understand where to place the sensors 12. In addition, the interpretation phase 76 may be performed using inversion, as described herein.

Figure 5:
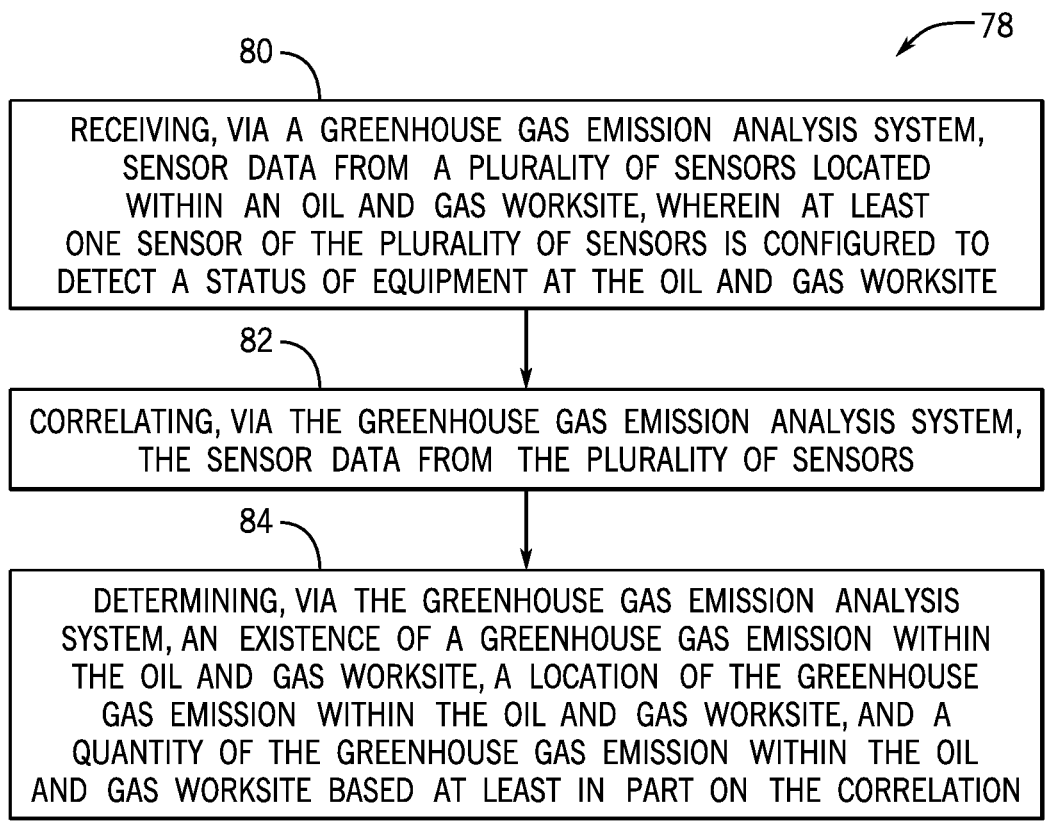
FIG. 5 is a flow diagram of a process for implementing the workflow of FIG. 4, in accordance with embodiments of the present disclosure.

FIG. 5 is a flow diagram of a process 78 for implementing the workflow 54 of FIG. 4. As described in greater detail herein, in certain embodiments, the process 78 may be implemented by the greenhouse gas emission analysis system 24 described herein. As illustrated in FIG. 5, in certain embodiments, the process 78 includes receiving, via the greenhouse gas emission analysis system 24, sensor data from a plurality of sensors 12 located within an oil and gas worksite 10, wherein at least one sensor of the plurality of sensors is configured to detect a status of equipment at the oil and gas worksite (block 80). In addition, in certain embodiments, the process includes correlating, via the greenhouse gas emission analysis system 24, the sensor data from the plurality of sensors 12 (block 82). In addition, in certain embodiments, the process 78 includes determining, via the greenhouse gas emission analysis system 24, an existence of a greenhouse gas emission within the oil and gas worksite 10, a location of the greenhouse gas emission within the oil and gas worksite 10, and a quantity of the greenhouse gas emission within the oil and gas worksite 10 based at least in part on the correlation (block 84). In addition, in certain embodiments, the process 78 includes identifying whether the greenhouse gas emission is a gas leak (e.g., unintentional) or a gas vent (e.g., intentional), for example, based at least in part on the correlation.

In addition, in certain embodiments, the process 78 optionally includes using, via the greenhouse gas emission analysis system 24, computational fluid dynamics (CFD) modeling 62 to determine the existence of the greenhouse gas emission within the oil and gas worksite 10, the location of the greenhouse gas emission within the oil and gas worksite 10, and the quantity of the greenhouse gas emission within the oil and gas worksite 10. In addition, in certain embodiments, the process 78 optionally includes using, via the greenhouse gas emission analysis system 24, a digital twin model 72 and the CFD modeling 62 to determine the existence of the greenhouse gas emission within the oil and gas worksite 10, the location of the greenhouse gas emission within the oil and gas worksite 10, and the quantity of the greenhouse gas emission within the oil and gas worksite 10. In addition, in certain embodiments, the process 78 optionally includes correlating, via the greenhouse gas emission analysis system 24, the sensor data with a 3D model 58 of facilities at the oil and gas worksite 10.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

In the claims, means-plus-function clauses are intended to cover the structures described herein as performing the recited function and not only structural equivalents, but also equivalent structures. Thus, for example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The invention claimed is:

1. A method, comprising:
    automatically sending, from a greenhouse gas emission analysis system, a control signal to a mobile platform to request that the mobile platform autonomously maneuver at least one sensor of a plurality of sensors located at different locations within an oil and gas worksite proximate a potential greenhouse gas emission within the oil and gas worksite;
    receiving, via the greenhouse gas emission analysis system, sensor data from the plurality of sensors, wherein each of the plurality of sensors are configured to detect different types of sensor data;
    correlating, via the greenhouse gas emission analysis system, the different types of sensor data from the plurality of sensors;
    determining, via the greenhouse gas emission analysis system, an existence of a greenhouse gas emission within the oil and gas worksite, a location of the greenhouse gas emission within the oil and gas worksite, and a quantity of the greenhouse gas emission within the oil and gas worksite based at least in part on the correlation of the different types of sensor data;
    identifying, via the greenhouse gas emission analysis system, whether the greenhouse gas emission is a gas leak or a gas vent based at least in part on the correlation of the different types of sensor data; and
    in response to identifying that the greenhouse gas emission is a gas leak, automatically sending, via the greenhouse gas emission analysis system, one or more control signals to one or more pieces of equipment of the oil and gas worksite to automatically adjust one or more operational parameters of the one or more pieces of equipment to minimize effects of the gas leak.

2. The method of claim 1, wherein the plurality of sensors comprises one or more flare monitors located within the oil and gas worksite, and wherein the sensor data collected by the one or more flare monitors relates to temperature and/or light measured proximate to one or more flares located within the oil and gas worksite.

3. The method of claim 1, wherein the plurality of sensors comprises one or more contact sensors located within the oil and gas worksite, and wherein the sensor data collected by the one or more contact sensors relates to whether one or more hatches of one or more storage tanks located within the oil and gas worksite are open or closed.

4. The method of claim 1, wherein the plurality of sensors comprises one or more compressor health monitors located within the oil and gas worksite, and wherein the sensor data collected by the one or more compressor health monitors relates to one or more operational statuses of valves, seals, motors, or other equipment associated with one or more compressors located within the oil and gas worksite.

5. The method of claim 1, wherein the plurality of sensors comprises one or more process monitors located within the oil and gas worksite, and wherein the sensor data collected by the one or more process monitors relates to one or more operational parameters relating to one or more processes occurring at the oil and gas worksite.

6. The method of claim 1, comprising autonomously maneuvering the at least one sensor of the plurality of sensors around the oil and gas worksite using the mobile platform based at least in part on the control signal sent by the greenhouse gas emission analysis system.

7. The method of claim 1, comprising using, via the greenhouse gas emission analysis system, computational fluid dynamics (CFD) modeling to determine the existence of the greenhouse gas emission within the oil and gas worksite, the location of the greenhouse gas emission within the oil and gas worksite, and the quantity of the greenhouse gas emission within the oil and gas worksite.

8. The method of claim 7, comprising using, via the greenhouse gas emission analysis system, a digital twin model and the CFD modeling to determine the existence of the greenhouse gas emission within the oil and gas worksite, the location of the greenhouse gas emission within the oil and gas worksite, and the quantity of the greenhouse gas emission within the oil and gas worksite.

9. The method of claim 1, comprising correlating, via the greenhouse gas emission analysis system, the sensor data from the plurality of sensors using one or more reduced order models (ROMs) that reduce computational complexity of computational fluid dynamics (CFD) model simulations of previously collected data relating to operation of the oil and gas worksite.

10. The method of claim 1, comprising correlating, via the greenhouse gas emission analysis system, the sensor data with a three-dimensional model of facilities at the oil and gas worksite.

11. The method of claim 1, wherein the greenhouse gas emission analysis system is an edge device that is part of a cloud-based computing environment.

12. The method of claim 1, wherein the plurality of sensors comprises one or more structural monitors located within the oil and gas worksite, and wherein the sensor data collected by the one or more structural monitors comprises three-dimensional mapping data of facilities at the oil and gas worksite.

13. The method of claim 1, wherein the plurality of sensors comprises one or more gas concentration monitors located within the oil and gas worksite, and wherein the sensor data collected by the one or more gas concentration monitors comprises gas concentration data.

14. The method of claim 1, wherein the plurality of sensors comprises one or more meteorological sensors located within the oil and gas worksite, and wherein the sensor data collected by the one or more meteorological sensors comprises meteorological data.

15. The method of claim 1, wherein correlating, via the greenhouse gas emission analysis system, the different types of sensor data from the plurality of sensors comprises triangulating respective locations of the plurality of sensors within the oil and gas worksite.

16. An edge device that is part of a cloud-based computing environment, the edge device comprising:
a greenhouse gas emission analysis system configured to:
automatically send a control signal to a mobile platform to request that the mobile platform autonomously maneuver at least one sensor of a plurality of sensors located at different locations within an oil and gas worksite proximate a potential greenhouse gas emission within the oil and gas worksite;
receive sensor data from the plurality of sensors, wherein each of the plurality of sensors are configured to detect different types of sensor data;
correlate the different types of sensor data from the plurality of sensors using one or more reduced order models (ROMs) that reduce computational complexity of computational fluid dynamics (CFD) model simulations of previously collected data relating to operation of the oil and gas worksite;
use the CFD model simulations to determine an existence of a greenhouse gas emission within the oil and gas worksite, a location of the greenhouse gas emission within the oil and gas worksite, and a quantity of the greenhouse gas emission within the oil and gas worksite based at least in part on the correlation of the different types of sensor data;
identify whether the greenhouse gas emission is a gas leak or a gas vent based at least in part on the correlation of the different types of sensor data; and
in response to identifying that the greenhouse gas emission is a gas leak, automatically send one or more control signals to one or more pieces of equipment of the oil and gas worksite to automatically adjust one or more operational parameters of the one or more pieces of equipment to minimize effects of the gas leak.

17. The edge device of claim 16, wherein the greenhouse gas emission analysis system is configured to use a digital twin model and the CFD model simulations to determine the existence of the greenhouse gas emission within the oil and gas worksite, the location of the greenhouse gas emission within the oil and gas worksite, and the quantity of the greenhouse gas emission within the oil and gas worksite.

18. The edge device of claim 16, wherein the greenhouse gas emission analysis system is configured to triangulate respective locations of the plurality of sensors within the oil and gas worksite to correlate the different types of sensor data from the plurality of sensors.

19. A system, comprising:
a plurality of discrete sensors located at different locations within an oil and gas worksite, wherein each of the plurality of discrete sensors are configured to detect different types of sensor data; and
a greenhouse gas emission analysis system configured to:
automatically send a control signal to a mobile platform to request that the mobile platform autonomously maneuver at least one discrete sensor of the plurality of discrete sensors proximate a potential greenhouse gas emission within the oil and gas worksite;
receive sensor data from the plurality of discrete sensors to correlate different types of the sensor data from the plurality of discrete sensors using one or more reduced order models (ROMs) that reduce computational complexity of computational fluid dynamics model simulations of previously collected data relating to operation of the oil and gas worksite;
determine an existence of a greenhouse gas emission within the oil and gas worksite, a location of the greenhouse gas emission within the oil and gas worksite, and a quantity of the greenhouse gas emission within the oil and gas worksite based at least in part on the correlation of the different types of sensor data;
identify whether the greenhouse gas emission is a gas leak or a gas vent based at least in part on the correlation of the different types of sensor data; and
in response to identifying that the greenhouse gas emission is a gas leak, automatically send one or more control signals to one or more pieces of equipment of the oil and gas worksite to automatically adjust one or more operational parameters of the one or more pieces of equipment to minimize effects of the gas leak.

20. The system of claim 19, wherein the greenhouse gas emission analysis system is configured to triangulate respective locations of the plurality of discrete sensors within the oil and gas worksite to correlate the different types of sensor data from the plurality of discrete sensors.

\* \* \* \* \*